(12) United States Patent
Yui

(10) Patent No.: US 7,905,374 B2
(45) Date of Patent: Mar. 15, 2011

(54) BOTTLED WATER COOLER WITH HOT WATER STERILIZATION SYSTEM

(76) Inventor: George Yui, Beilum (CN)

( * ) Notice: Subject to any disclaimer, the term of this patent is extended or adjusted under 35 U.S.C. 154(b) by 699 days.

(21) Appl. No.: 11/773,063

(22) Filed: Jul. 3, 2007

(65) Prior Publication Data

US 2008/0093385 A1  Apr. 24, 2008

(51) Int. Cl.
 *B67D 1/00* (2006.01)
(52) U.S. Cl. ............ 222/67; 222/146.1; 222/185.1
(58) Field of Classification Search ............ 222/67, 222/148, 146.1, 185.1; 210/175, 416.3; 137/15.26, 137/41, 101.27
See application file for complete search history.

(56) References Cited

U.S. PATENT DOCUMENTS

| | | | | |
|---|---|---|---|---|
| 1,079,918 A | * | 11/1913 | Long et al. ............ 62/188 |
| 1,501,068 A | * | 7/1924 | Schatz ............ 222/67 |
| 1,591,799 A | * | 7/1926 | Tinapp ............ 137/433 |
| 2,747,605 A | * | 5/1956 | Adams ............ 73/322.5 |
| 2,912,142 A | * | 11/1959 | Schultz ............ 222/129 |
| 3,468,370 A | * | 9/1969 | Castillo ............ 165/66 |
| 3,698,603 A | * | 10/1972 | Radcliffe ............ 222/146.1 |
| 3,915,341 A | * | 10/1975 | Brown ............ 222/67 |
| 5,667,103 A | * | 9/1997 | Donselman et al. ............ 222/129 |
| 6,143,258 A | * | 11/2000 | Tamura et al. ............ 422/307 |
| 6,207,046 B1 | * | 3/2001 | Yamashita et al. ............ 210/138 |

* cited by examiner

*Primary Examiner* — Kenneth Bomberg
*Assistant Examiner* — Daniel R Shearer
(74) *Attorney, Agent, or Firm* — Michael Ries

(57) ABSTRACT

The present invention is a bottled water cooler with a hot water sterilization system. A bottled water cooler with a hot water sterilizing system having a cold tank installed on the top of the cooler. There is a bottle receptacle in it, and the bottle receptacle groove having a probe connecting with water bottle and the cold tank inside. There is a baffle on a hollow baffle leader under the probe. The end of the baffle leader connects with a hot tank installed under cold tank by the cold and hot tank connecting tube, hot tank draining three-way pipe or draining pipe.

6 Claims, 4 Drawing Sheets

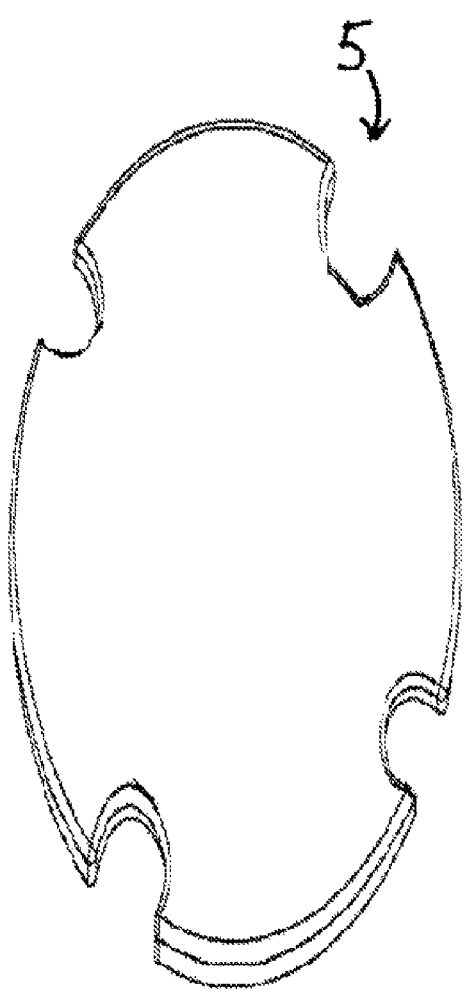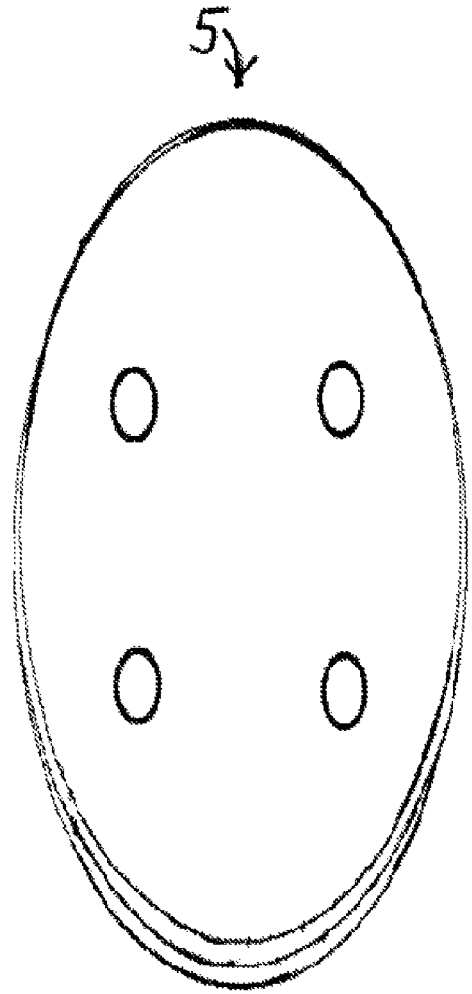
Figure 3                               Figure 4

BOTTLED WATER COOLER WITH HOT WATER STERILIZATION SYSTEM

This application claims the benefit of Chinese Patent Application No. 200620105324.2 filed Jul. 3, 2006 Titled BOTTLED WATER COOLER WITH HOT WATER STERILIZATION SYSTEM, George Yui inventor.

TECHNICAL FIELD & BACKGROUND

The present invention generally relates to the field of bottled water coolers, more specifically a kind of bottled water cooler with a hot water sterilization system, mainly used for home or office.

Presently, most of the coolers on the market do not have sterilization systems. Without sterilization, bacteria builds up inside of the cooler. The water becomes contaminated and can be harmful to the user's health. Others invented water coolers with sterilization systems, for example Chinese patent No. 200420081793.6, which is a type of bottled water cooler with an ozone sterilizing system. It contains a water bottle and a cold water tank. In this cooler, an ozonator is set up outside of the cold water tank, and ozone emanating equipment is set up on the bottom inside of the cold water tank. They are connected by a flexible connecting tube. The disadvantage of this kind of cooler is that it is complicated in structure. Installation of the ozonator and ozone emanation equipment is also difficult, increasing production cost. Unless the cooler has proper seals, and a way to deactivate the ozone, maintaining legal ozone emission levels is also difficult.

The present invention is a bottled water cooler with a hot water sterilizing system its structure is simple allowing the present invention to be cleaned less often. The present invention can sterilize by water convection in the cold and hot tank slowing the increase in bacteria and ultimately preventing bacteria.

The present invention is a bottled water cooler with a hot water sterilizing system having a cold tank installed on the top of the cooler. There is a bottle receptacle in it. This bottle receptacle has a probe connecting with the water bottle and the cold tank inside. There is a baffle attached to a hollow baffle leader under the probe. The end of this baffle leader connects with the hot tank installed under the cold tank by a cold and hot tank connecting tube, a hot tank draining three-way pipe and draining pipe. They set up a baffle for the cold tank between the cold and hot tank. The hot tank has a hot tank outlet and a hot tank exhaust tube between the cold and hot tank. There is also a straight tube with a valve that connects the cold and hot tank.

Inside of the probe is a check floating seal fitting. The check floating seal fitting is made up of floating board, restricting bolts and mat piece which can prevent the floating board from falling off. The floating board is a thin disk shape and there is circular groove on it. The check floating seal fitting is made up of a float and rail on the probe. The rail can prevent the float from falling off. On the float, there is a fixed round seal ring or in the probe there is a fixed circular seal ring. The check floating seal fitting is made up of a protruding shaped float and rail which is on the probe and can prevent the float from falling off. On the float protruding disk, securing a round seal ring or inside the probe securing a circular seal ring. The float is solid or hollow. The stated valve is a solenoid valve or an electrical valve.

In the present invention, in between the cold and hot tank is a straight connecting tube. The heated water, using convection principles, enters into the cold tank through this tube, and sterilizes the cold tank using high temperatures. Also, the check floating structure installed on the bottle receptacle can prevent the water in the bottle from convecting to hot water, thereby preventing water in the bottle from being heated and wasting the bottled water.

BRIEF DESCRIPTION OF THE DRAWINGS

The present invention will be described by way of exemplary embodiments, but not limitations, illustrated in the accompanying drawings in which like references denote similar elements, and in which:

FIG. 3 a is a top view of a floating board, in accordance with one embodiment of the present invention;

FIG. 4 a is a bottom view of a floating board, in accordance with one embodiment of the present invention;

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention; however, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figures 1, 2:
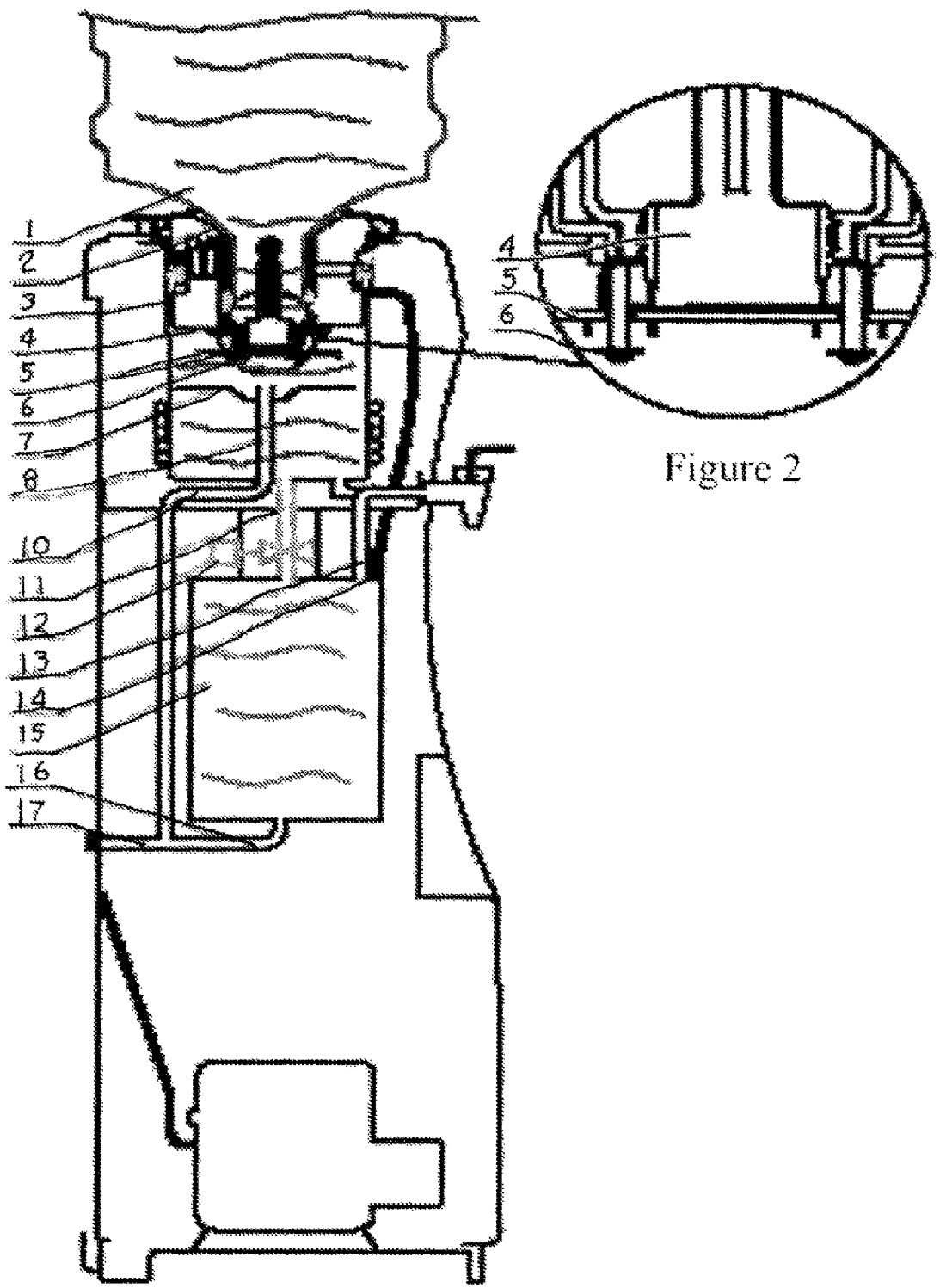
FIG. 1 is a sectional view of a bottled water cooler, in accordance with one embodiment of the present invention.
FIG. 2 an exploded view of a probe, floating board and seal, in accordance with one embodiment of the present invention.

Now referring to FIG. 1 and FIG. 2 as in one embodiment of the present invention, shown is a side sectional view of a bottled water cooler and an exploded view of a particular area of the bottled water cooler. Shown is a cold tank 3 installed on the top of a cooler, inside of cold tank 3 there is a bottle receptacle 2, and on the top of cold tank 3 there is a check valve structure which can efficiently prevent water from overflowing from the cooler due to a cracked water bottle 1. Inside of the groove of the stated bottled receptacle 2 is a probe 4 connecting with water bottle 1. Inside of the probe 4 is a check floating seal fitting. In this example, the stated floating seal fitting is made up of floating board 5 and screws which can prevent floating board 5 from falling off and mat piece or seal 6.

Referring to FIG. 3 and FIG. 4 as in one embodiment of the present invention, shown in FIG. 3 is a top view of floating board 5 and in FIG. 4 is a bottom view of floating board 5. Floating board 5 is a thin disc shape made of polypropylene. Its specific gravity is 0.97. This is a little less than the specific gravity of water. This way the floatage of the floating board 5 is very small, so it is not fast when closing and opening in place. The floating board 5 has no resistance when the opening place opens, it will not prevent water flowing fast when floating board 5 seals the opening place too fast due to big floatage. This allows the floating board 5 in cold tank 3 to close the passage of the probe 4 when the water level reaches a certain height. When the water lever drops when using water in the cooler, the floating board 5 moves down due to gravity, which opens the passage of the probe 4. When the water enters the cold tank 3, and the water level reaches a certain height, the floating board 5 closes the passage of the probe 4. This way it can prevent water from entering the water bottle 1 when the hot water comes into the cold tank 3 during sterilization. This prevents the water in the water bottle 1 from being heated, saving the bottled water. Also, to avoid the floating board 5 from sticking to the probe 4 due to molecule gravitation, the floating board 5 must be bigger than the opening of the probe 4. There is a circular groove on the center part of the floating board 5. It can reduce the distortion of the floating board 5 due to high temperature. Also providing a sealing for the flat surface on the edge of the ridge of the bottom of bottle receptacle 2. The stated cold tank 3 inside, and under the probe 4, there is a baffle 7 on the hollow baffle leader. The baffle 7 separates the cold tank 3 into 2 separate water levels. The baffle leader end and hot tank 15 under the cold tank 3 connect through the cold and hot tank connecting tube 10, hot tank drain three-way pipe 17 and hot tank inlet or outlet 16. Cold water can flow to the hot tank 15 through this passage from cold tank 3. Between the cold tank 3 and the hot tank, there is a cold tank tube 11, and there is valve 12 on it. In this example the valve 12 is a solenoid valve (the stated valve 12 also can be an electrical valve), controlled by a microprocessor to open and close. Usually when the solenoid is closed, to sterilize the cold tank 3, the microprocessor will give a signal to open the solenoid. Hot water enters the cold tank 3 to sterilize with high temperature water through the cold and hot tank tube 11. Between the cold tank 3 and hot tank 15 there is a cold tank baffle 8. On top of the stated hot tank 15 there is a hot tank outlet tube 13 and a hot tank vent-pip To sterilize as in one embodiment of the present invention under normal uses of the cooler the cold tank 3 and hot tank 15 all have full water, and the valve 12 is open; when there is a need to sterilize the cold tank 3, the microprocessor closes the refrigeration system, and opens the valve 12. Now using cold and hot water convection principles, the present invention makes water in cold tank 3 hot by convection in hot tank 15. Hot water in the hot tank 15 enters the cold tank 3 through the tube 11. Cold water in the cold tank 3 enters the hot tank 15 through the hot and cold tank tube. At the same time the hot tank 15 heats the water whose temperature is low, and continues to circulate it, until the temperature in the cold tank 3 reaches 84C. Then the microprocessor restarts the cold tank system and closes the valve 12, cutting off the convection passage or tube 11. Now the cooler recovers to its normal state. For convenience we can set up times and periods to sterilize the cooler through the microprocessor.

Figure 5:
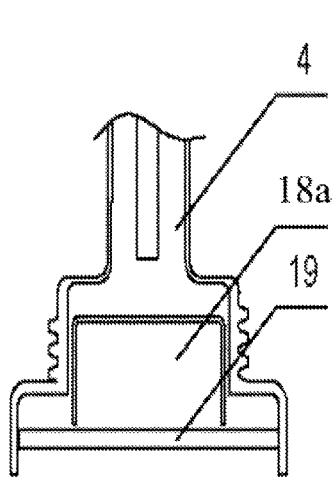
FIG. 5 a is a section view of the check floating structure, in accordance with one embodiment of the present invention.
Figure 6:
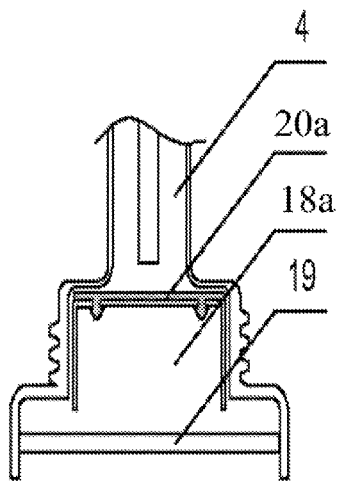
FIG. 6 a is a section view of the check floating structure, in accordance with one embodiment of the present invention.
Figure 7:
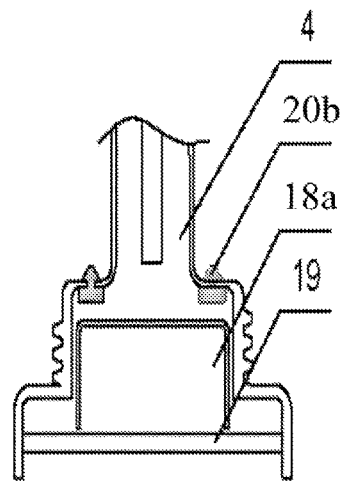
FIG. 7 a is a section view of the check floating structure, in accordance with one embodiment of the present invention.

Referring to FIG. 5 as in one embodiment of the present invention, shown is a check floating seal fitting, which is made up of float 18*a*, and rail 19 on the probe 4. The rail can prevent the float from falling off. Referring to FIG. 6 as in one embodiment of the present invention, shown is a set, a round seal ring 20*a* on float 18*a*. Referring to FIG. 7 as in one embodiment of the present invention, shown is a fixed round seal ring 20*b* in the probe 4.

Figure 8:
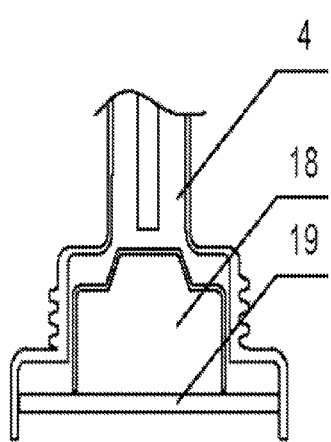
FIG. 8 a is a section view of the check floating structure, in accordance with one embodiment of the present invention.
Figure 9:
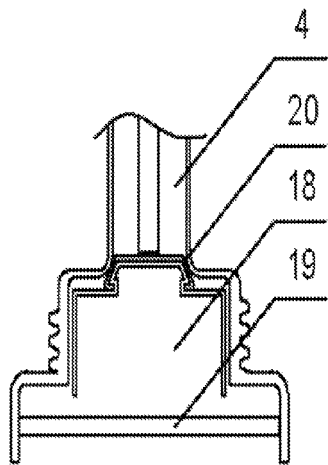
FIG. 9 a is a section view of the check floating structure, in accordance with one embodiment of the present invention.
Figure 10:
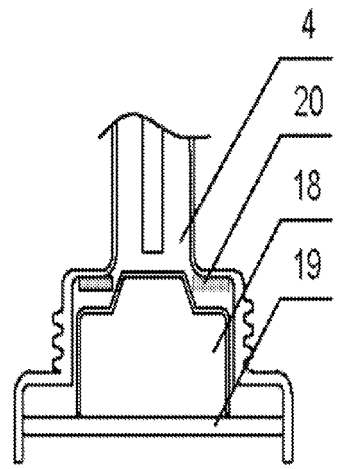
FIG. 10 a is a section view of the check floating structure, in accordance with one embodiment of the present invention.

Referring to FIG. 8 as in one embodiment of the present invention, shown is the stated check floating seal fitting. It is a protruding shaped float 18*b* and rail 19 which is on the probe that prevents the float falling off. Referring to FIG. 9 as in one embodiment of the present invention, shown is a set seal ring 20*c* on a protruding table of shaped float 18*b*. Referring to FIG. 10 as in one embodiment of the present invention, shown is the probe 4 securing a circular seal ring 20*d*.

The float 18*a* and the protruding shaped float 18*d* are made of food grade plastic which density is smaller than water and can be solid or hollow. The sterilization process in the same in all cases.

While the present invention has been related in terms of the foregoing embodiments, those skilled in the art will recognize that the invention is not limited to the embodiments depicted. The present invention can be practiced with modification and alteration within the spirit and scope of the appended claims. Thus, the description is to be regarded as illustrative instead of restrictive on the present invention.

What is claimed is:

1. A bottled water cooler with hot water sterilizing system comprising:
    a water bottle,
    a cold tank installed on top of the bottled water cooler, the bottled water cooler having a bottle receptacle with a bottle receptacle groove, said groove having a probe connecting with said water bottle,
    the cold tank having a baffle with a hollow baffle leader located under the probe, one end of the baffle leader connected to a hot tank connecting tube,
    a hot tank installed under the cold tank,
    the hot tank connecting tube connected to a three way pipe, said three way pipe comprising a draining pipe and a hot tank inlet or hot tank draining pipe,
    a tank baffle located between the cold tank and the hot tank,
    the hot tank having a hot tank outlet,
    a hot tank exhausting tube connected to the hot tank and the cold tank with a valve within said hot tank exhausting tube for opening and closing said hot tank exhausting tube,
    a check floating seal fitting which includes a floating board which has a specific gravity of less than water and greater than 0.96 for selectively sealing an opening of the probe.

2. The bottled water cooler with hot water sterilizing system of claim 1 wherein the check floating seal fitting further includes restricting bolts which can prevent the floating board from falling off a mat piece.

3. The bottled water cooler with hot water sterilizing system of claim 1 wherein the floating board is thin disk shaped and there is circular groove on it.

4. The bottled water cooler with hot water sterilizing system of claim 1 wherein the stated float is solid.

5. The bottled water cooler with hot water sterilizing system of claim 1 wherein the valve is a solenoid valve.

6. The bottled water cooler with hot water sterilizing system of claim 1 wherein the valve is an electrical valve.

* * * * *